(12) United States Patent
Kirsch et al.

(10) Patent No.: US 11,034,913 B2
(45) Date of Patent: Jun. 15, 2021

(54) METAL WORKING FLUID

(71) Applicant: Henkel AG & Co. KGaA, Duesseldorf (DE)

(72) Inventors: Gabriel J. Kirsch, Strongsville, OH (US); Christine Zarzycki, Farmington Hills, MI (US)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/009,756

(22) Filed: Jun. 15, 2018

(65) Prior Publication Data

US 2018/0291306 A1 Oct. 11, 2018

Related U.S. Application Data

(63) Continuation of application No. PCT/US2016/063896, filed on Nov. 29, 2016.

(60) Provisional application No. 62/387,458, filed on Dec. 23, 2015.

(51) Int. Cl.
| | |
|---|---|
| *C10M 173/02* | (2006.01) |
| *A01N 33/04* | (2006.01) |
| *C10M 133/06* | (2006.01) |
| *A61L 2/18* | (2006.01) |
| *C10M 133/12* | (2006.01) |
| *C10M 173/00* | (2006.01) |
| *C10M 133/10* | (2006.01) |
| *C10N 30/10* | (2006.01) |
| *C10N 30/16* | (2006.01) |
| *C10N 40/20* | (2006.01) |
| *B23Q 11/10* | (2006.01) |

(52) U.S. Cl.
CPC ......... *C10M 173/02* (2013.01); *A01N 33/04* (2013.01); *A61L 2/18* (2013.01); *C10M 133/06* (2013.01); *C10M 133/10* (2013.01); *C10M 133/12* (2013.01); *C10M 173/00* (2013.01); *B23Q 11/1061* (2013.01); *C10M 2201/02* (2013.01); *C10M 2203/1006* (2013.01); *C10M 2207/046* (2013.01); *C10M 2207/12* (2013.01); *C10M 2207/123* (2013.01); *C10M 2207/125* (2013.01); *C10M 2207/126* (2013.01); *C10M 2207/127* (2013.01); *C10M 2209/108* (2013.01); *C10M 2215/04* (2013.01); *C10M 2215/042* (2013.01); *C10M 2215/08* (2013.01); *C10M 2215/223* (2013.01); *C10M 2215/26* (2013.01); *C10M 2215/28* (2013.01); *C10M 2215/30* (2013.01); *C10M 2223/04* (2013.01); *C10M 2229/02* (2013.01); *C10N 2030/10* (2013.01); *C10N 2030/16* (2013.01); *C10N 2040/20* (2013.01)

(58) Field of Classification Search
CPC ............ C10N 2230/44; C10N 2230/24; C10N 2230/18; C10N 2230/12; C10N 2030/12; C10N 2030/04; C10N 2030/18; C10N 2240/40; C10N 2210/01; C10N 2040/20; C10M 2207/04; C10M 2223/06; C10M 2215/064; C10M 2207/127; C10M 2203/1006; C10M 2207/021; C10M 2207/126; C10M 2207/128; C10M 2207/142; C10M 2207/18; C10M 2209/103; C10M 2215/04; C10M 2215/042; C10M 2215/06; C10M 2215/082; C10M 2215/223; C10M 2217/046; C10M 2219/02; C10M 2223/04; C10M 2215/30; C10M 2219/09; C10M 2201/062

See application file for complete search history.

(56) References Cited

U.S. PATENT DOCUMENTS

| | | | |
|---|---|---|---|
| 5,132,046 A | 7/1992 | Edebo et al. | |
| 5,633,222 A | 5/1997 | Skold et al. | |
| 5,723,418 A | 3/1998 | Person Hei et al. | |
| 5,863,874 A | 1/1999 | Person Hei et al. | |
| 5,932,526 A | 8/1999 | Person Hei et al. | |
| 6,214,777 B1 | 4/2001 | Li et al. | |
| 7,595,288 B2 | 9/2009 | Fretz et al. | |
| 2002/0016266 A1* | 2/2002 | Fletschinger | C10M 129/18 508/433 |
| 2005/0107270 A1* | 5/2005 | Gernon | C10M 173/02 508/562 |
| 2009/0291867 A1 | 11/2009 | Fretz et al. | |
| 2010/0264359 A1 | 10/2010 | Straetmans et al. | |
| 2012/0184475 A1* | 7/2012 | Takagi | C10M 173/00 508/505 |

FOREIGN PATENT DOCUMENTS

| | | |
|---|---|---|
| CA | 2496230 A1 | 8/2005 |
| CN | 1694622 A | 11/2005 |
| CN | 101522875 A | 9/2009 |
| CN | 103108837 A | 5/2013 |
| GB | 1330531 A | 9/1793 |
| GB | 2016516 A | 9/1979 |

(Continued)

OTHER PUBLICATIONS

International Search Report for PCT/US2016/063896, dated Mar. 23, 2017.

(Continued)

*Primary Examiner* — Vishal V Vasisth
(74) *Attorney, Agent, or Firm* — Mary K. Cameron

(57) ABSTRACT

Aqueous metal working fluids, concentrates thereof, and processes to reduce the presence of *Mycobacterium* in the aqueous metal working fluids, or in a metal working environment.

23 Claims, No Drawings

(56) References Cited

FOREIGN PATENT DOCUMENTS

| | | |
|---|---|---|
| GB | 2292687 A | 3/1996 |
| JP | 02228394 A | 9/1990 |
| JP | H2228394 A | 9/1990 |
| JP | 2000226594 A | 8/2000 |
| RU | 2456022 C1 | 7/2012 |
| WO | 9412028 A1 | 6/1994 |
| WO | 2014084171 A1 | 6/2014 |
| WO | 2017112113 A1 | 6/2017 |

OTHER PUBLICATIONS

Bogatcheva E. et al, "Identification of new diamine scaffolds with activity against *Mycobacterium tuberculosis*", J. Med. Chem., Jun. 1, 2006, 49 (11), pp. 3045-3048—Cited in International Search Report dated Mar. 23, 2017 for corresponding PCT application PCT/US2016/063896.

Supplementary European Search Report for EP 16879837 dated May 14, 2019.

\* cited by examiner

METAL WORKING FLUID

This application is a CON of PCT/US2016/063896, filed Nov. 29, 2016 which claims benefit of 62/387,458 filed Dec. 23, 2015.

BACKGROUND OF THE INVENTION

1. Field of the Invention

The present invention pertains to metal working fluids and their uses. More particularly, the present invention relates to aqueous alkaline metal working fluids and concentrates thereof and processes for their use while diminishing the likelihood of microbial proliferation. The processes reduce the presence of *Mycobacterium* in aqueous alkaline metal working fluids or in a metal working environment.

2. Description of the Related Art

The increasing cost and disposal problems of non-aqueous, oil-based functional fluid compositions has accelerated the demand for aqueous-based functional fluid compositions. Aqueous-based metal working fluids have been gaining in importance over non-aqueous metal working fluids because of their economic, environmental, and safety advantages. Water-based metal working fluids have been used in chip forming and non-chip forming metal working processes well known in the art such as drilling, tapping, broaching, grinding, rolling, drawing, spinning, milling, bending, turning, and stamping.

Typically, metal working fluids are used in open systems and are exposed to bacteria and other microorganisms. It has been recognized that certain fast-growing bacteria affect fluid performance in use or during extended storage. Use of antimicrobials in aqueous alkaline industrial fluids to reduce the deterioration of fluid performance caused by microbial action on fluid components over time is known in some circumstances.

Besides affecting fluid performance, certain types of slow-growing bacteria, such as *Mycobacterium*, have been linked to health problems associated with occupational exposure to metal working fluids, including occupational asthma, bronchitis, hypersensitivity pneumonitis, as well as eye irritation, skin rashes, etc., as *Mycobacterium* may become aerosolized when the metal working fluid is sprayed. *Mycobacterium* present a problem due to its relatively high degree of intrinsic resistance to most antibiotics and chemotherapeutic agents. *Mycobacterium*, as used herein, refers to the *Mycobacterium* genus in general.

*Mycobacterium* is more resistant than most other bacteria due to a complex cell wall that contains unusual lipids and functions as a permeability barrier. The cell wall distinguishes *Mycobacterium* species, including the human pathogen *Mycobacterium tuberculosis*, from other Gram-positive bacteria. The low permeability of the cell wall, with its unusual structure, appears to be a major factor contributing to the resistance. Hydrophilic agents tend to cross the cell wall slowly because the mycobacterial porin is present in only low concentrations and is generally inefficient in allowing the permeation of solutes. Lipophilic agents are presumably slowed down by the lipid bilayer which is of unusually low fluidity and abnormal thickness.

While at first, *Mycobacterium* may not be present in a significant amount in metal working fluids, as it tends to be "out-competed" by other microorganisms in ordinary environments, this dynamically changes with time due to addition of biocides designed to eliminate common bacteria. Bacteria susceptible to the biocides are reduced in population, and *Mycobacterium* begins to increase in titer amount. Thus generally, biocide/biostat additives effective for common bacteria create a favorable environment for the highly resistant *Mycobacterium*. Such exemplary biocides include formalin or formaldehyde compounds.

Additionally, numerous biocide substances can also be potentially harmful to human populations and the environment. For example, triazine was a common metal working biocide for controlling bacterial growth with good efficacy. But triazine has been linked to hypersensitivity pneumonitis with coolant users and has also faced greater scrutiny from the EPA as a formaldehyde condensate. Therefore, it continues to be phased out from metal working fluid usage. Other formalin-based and formaldehyde-based biocides present serious health concerns due to their carcinogenicity and high volatility. Elevated working temperatures experienced in some metal working processes may lead to substantial volatilization of formalin or formaldehyde or breakdown of formalin precursors, requiring routine reintroduction of these compounds into the working fluid. In addition, in open systems, and in particular those systems that generate aerosols, such as metal working environments, worker exposure is a concern.

Elimination of these compounds from the metal working fluids has resulted in use of other, relatively less effective or less stable alternative biocides. Yet, frequently, an additional tankside biocide must be added to maintain low bacterial growth in large and small central system tanks. This tankside biocide usage can present problems with inventory and operator health and safety.

Attempts have also been made to combat *Mycobacterium* using compounds that interfere with the metabolism of the bacteria itself. Unfortunately, these substances can also be typically harmful to people. Examples of such compounds include chlorinated phenols, isothiazolinones, and dicyclohexylamine, which have been found to have some efficacy against *Mycobacterium* under certain circumstances. Yet, their utilization in metal working fluid operations and environments is hampered by drawbacks in the areas of worker safety, wastewater management, or stability. For example, chlorinated phenols are highly regulated by the EPA in waste streams. Isothiazolinones are expensive, sensitizing agents to tissue, and are not stable in alkaline environments. Pure dicyclohexylamine is toxic by ingestion and absorption and corrosive to the respiratory system. Additionally, dicyclohexylamine is a secondary amine, and thus a potential precursor for carcinogenic nitrosamines which can form while the metal working fluid is stored for long periods of time. In general, secondary amines are thus not desirable for purposes of eliminating or slowing down growth of *Mycobacterium* in the metal working fluids.

As a means of extending fluid life and performance, certain secondary alkanolamines have been employed as antimicrobial agents to reduce component deterioration by *Pseudomonas* or *Fusarium* species, as disclosed by R. Skold and P. Raune, U.S. Pat. No. 5,633,222 and by L. Edebo and M. Sandin, U.S. Pat. No. 5,132,046. Certain antimicrobial lubricants that include an alkyl ether amine component have found use in food or beverage container conveyor systems. It has been proposed that these lubricants are useful in reducing slime formation caused by microbial action on food residues, thus improving conveyor performance, as disclosed by Hei, et al. U.S. Pat. No. 5,863,874; Hei, et al. U.S. Pat. No. 5,723,418; and Hei et al. U.S. Pat. No. 5,932,526.

The extent of broad spectrum antimicrobial activity and the level of efficacy for the general class of ether amines appear unpredictable. Hei, et al. U.S. Pat. No. 5,863,874 and Li, et al. U.S. Pat. No. 6,214,777 each disclose lubricating compositions which may include an ether amine for use in conveyor systems where external stresses, such as working temperature or working pressure, are minimal. In Hei, et al. U.S. Pat. No. 5,863,874, certain ether amines are alleged to have ascertainable activity against some microorganisms under certain conditions. Under similar working conditions, Li et al. U.S. Pat. No. 6,214,777 disclose certain ether amines at much increased loadings which require a quaternary phosphonium compound as an antimicrobial to achieve the desired effect. External stresses such as elevated temperatures or pressures imposed by the working environment of processes such as metal working may further impact efficacy of certain ether amines through undesired thermal degradation, side reactions, volatilization, and the like. Under working conditions with increased external stresses, it is difficult to predict whether certain ether amines would have broad spectrum activity, a more limited range of activity against some microorganisms, or no activity at all.

Fretz et al., U.S. Pat. No. 7,595,288 disclose an aqueous alkaline metal working fluid comprising certain alkyl ether amines. While the disclosed alkyl ether amines have provided relatively good biostatic results with respect to *Mycobacterium*, the alkyl ether amines can be difficult to formulate into water-based products, probably due to the presence of both amine and ether functional groups. Additionally, the metal working fluids including the alkyl ether amines exhibit an objectionable odor which requires special handling procedures. The odor is believed to be present due to residual alcohol leftover from the production of the ether amine.

Therefore, there has been a need to address failure of others to solve the above-mentioned problems. There has been a need to provide a non-toxic metal working fluid which would be free of a strong odor and which inhibits microbial growth including *Mycobacterium* in metal working fluids as well as metal working environments. Finally, there has been a need to develop an effective biostat for *Mycobacterium* which could be easily formulated into water-based metal working fluids.

SUMMARY OF EMBODIMENTS OF THE INVENTION

In at least one embodiment, the invention pertains to a metal working fluid comprising at least one amine of Formula Ia, Ib or Ic:

$$R_1 \diagup^{NH_2} \qquad \text{Formula Ia}$$

wherein each $R_1$ is independently $C_5$-$C_{10}$ alkyl, or $$H_2N \diagup^{R_2} \diagdown NH_2 \qquad \text{Formula Ib}$$

wherein $R_2$ is independently a linear or branched $C_5$-$C_8$ alkyl or $C_6$ cycloalkylene, or $$(NH_2CH_2CH_2)_3N, \qquad \text{Formula Ic:}$$

with the proviso that the at least one amine is not pentylamine, 1,2-cyclohexanediamine, 1,6-diaminohexane, or 1,3-pentanediamine, and preferably is not a secondary amine.

In at least one embodiment, the invention pertains to a process for reducing the concentration of *Mycobacterium* in an aqueous alkaline metal working environment, comprising providing to the metal working environment an aqueous metal working fluid incorporating an effective *Mycobacterium* inhibiting amount of at least one amine according to one of Formula Ia, Ib, and Ic, as described above.

In at least one embodiment, the invention pertains to a process for shaping a metal workpiece in the presence of a metal working fluid containing at least one amine of Formula Ia, Ib or Ic, as described above.

In various further embodiments of the above-described metal working fluids and processes, the invention may comprise one or a combination of the below recited features in any combination or number:

a) metal working fluid wherein each R1 of Formula Ia may independently be $C_6$-$C_8$ alkyl;

b) metal working fluid wherein each R2 of Formula Ib may independently $C_6$-$C_7$ alkyl;

c) metal working fluid wherein the $C_5$-$C_{10}$ alkyl in Formula Ia comprises dimethylhexyl, ethylhexyl, heptyl, or octyl;

d) metal working fluid comprising wherein the $C_5$-$C_8$ alkyl comprises pentamethylene and the $C_6$ cycloalkylene comprises cyclohexylene in Formula Ib;

e) metal working fluid comprising about 0.2 to 15 wt. %, preferably 1 to 7 wt. %, of the at least one amine, based on the total weight of the aqueous alkaline metal working fluid;

f) metal working fluid that is free of at least one of materials selected from amines comprising an ether group, triazine, boron, dicyclohexylamine and a combinations thereof;

g) metal working fluid comprising about 0.2 to 20 wt. % of acid-based pH buffer(s) and a non-zero amount up to 25 wt. % of organic amine pH buffer;

h) metal working fluid comprising water, at least one pH buffer, a biocide, an anti-foaming agent, and optionally a corrosion inhibitor, an emulsifier, or a lubricant additive; desirably about 0.05 to 2 wt. % of biocide(s), about 0.05 to 2 wt. % of anti-foaming agent(s), about 0.2 to 20 wt. % of pH buffer(s), a non-zero amount up to 25 wt. % of emulsifier(s), or a combination thereof, based on the total weight of the aqueous metal working fluid;

i) metal working fluid comprising a non-zero amount up to 50 wt. % of hydrodynamic lubricant additive(s), a non-zero amount up to 40 wt. % of boundary lubricant additive(s), and a non-zero amount up to 40 wt. % of extreme pressure lubricant additive(s);

j) metal working fluid comprising at least one corrosion inhibitor that comprises organic carboxylic acid having 12-16 carbon atoms, benzotriazole, sodium salt of tolyltriazole, or a combination thereof;

k) one or more of a cast iron corrosion inhibitor, a yellow metal corrosion inhibitor, or an aluminum corrosion inhibitor, desirably a non-zero amount up to 15 wt. % of cast iron corrosion inhibitor(s), a non-zero amount up to 5 wt. % of yellow metal corrosion inhibitor(s), and a non-zero amount up to 5 wt. % of aluminum corrosion inhibitor(s). based on the total weight of the aqueous metal working fluid.

DETAILED DESCRIPTION OF EMBODIMENTS OF THE INVENTION

The aqueous alkaline metal working fluid includes at least one amine of formula Ia, Ib, or Ic:

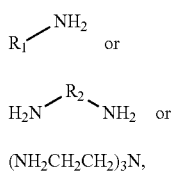

$$R_1 \diagup ^{NH_2} \quad \text{(Ia)}$$

or $$H_2N \diagup ^{R_2} \diagdown NH_2 \quad \text{(Ib)}$$

or $$(NH_2CH_2CH_2)_3N, \quad \text{(Ic)}$$

wherein $R_1$ in Formula Ia may be independently $C_2$-$C_{18}$ alkyl or $C_4$-$C_{16}$ alkyl. Alternatively, $R_1$ may be independently $C_5$-$C_{12}$ alkyl. Preferably, at least one $R_1$ is $C_6$-$C_8$ alkyl. Even more preferably, the amine of Formula Ia may be dimethylhexylamine, 2-ethylhexylamine, heptylamine, or octylamine.

$R_2$ in Formula Ib may be independently $C_5$-$C_8$ alkyl or $C_6$ cyclohexylene. Preferably, at least one $R_2$ is $C_7$-$C_8$ alkyl or cyclohexane. Even more preferably, the amine of Formula Ib may be 2-methylpentane-1,5-diamine or 1,4-cyclohexanediamine.

The at least one amine may be a primary amine or a tertiary amine or combination thereof. The amine is preferably free of ether groups. The primary amine may be mono- or di-primary amine. The primary amine in Formulas Ia and Ib may be linear, branched, or cyclic. The tertiary amine in Formula Ic includes primary amine end groups which may be aliphatic. The amine of formula Ic may be tris(2-aminoethyl)amine.

The metal working composition may include about 0.2 to 15 wt. % of the at least one amine of Formulas Ia, Ib, or Ic. Preferably, the amount of the at least one amine of the above-mentioned formulas is about 1 to 7 wt. %, even more preferably about 3 to 4 wt. %. The amount of the at least one amine of the above-mentioned formulas is at least, with increasing preference in the order given, about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6 or 3.8, wt. %, and not more than, with increasing preference in the order given, about 15, 14.5, 14.0, 13.5, 13.0, 12.5, 12.0, 11.5, 11.0, 10.5, 10.0, 9.5, 9.0, 8.5, 8.0, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, or 4.0 wt. %.

The aqueous alkaline metal working fluid may optionally contain various additives well known in the art such as for example extreme pressure additives, corrosion inhibitors, anti-foaming agents, surfactants, emulsifiers, boundary lubricant additives, hydrodynamic lubricant additives, pH buffers, biocides, film forming additives, anti-mist agents, humectants, thickeners, chelating agents, dyes, or the like. The compositions and usable concentrations of these additives are well known in the art and such compositions and concentrations may be optionally employed provided that their use does not interfere with the desired antimicrobial action.

Extreme pressure additives reduce tool wear while increasing work speed, thus making it possible to cut hard metals and increase production rates. The three distinct varieties of extreme pressure additives are phosphate esters, active sulfur (polysulfides), and chlorinated additives. Typical examples of extreme pressure additives include but are not limited to phosphate esters such as polyoxyethylene oleyl ether phosphate and other phosphates; polysulfides having one or more reduced sulfur atoms capable of forming metal sulfide such as di-tert-dodecyl polysulfides and di-tert nonyl polysulfides; and chlorinated hydrocarbon additives carbon based molecules with chlorine substituted for hydrogens, wherein the chlorine content in the molecule is usually greater than about 5% by weight. Chloroalkanes or chlorinated carboxylic acids, such as octadecanoic acid are typical examples of chlorinated hydrocarbon extreme pressure additives. The metal working fluid may comprise about 1 to 40 wt. %, more preferably about 1 to 5 wt. %, even more preferably, about 2 to 3 wt. % of extreme pressure additive(s). The metal working composition may include at least, with increasing preference in the order given, about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 wt. %, and not more than, with increasing preference in the order given, about 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4.9, 4.8, 4.6, 4.5, 4.4, 4.3, 4.2, 4.1, 4.0, 3.9, 3.8, 3.7, 3.6, 3.5, 3.4, 3.3 or 3.2 wt. % of extreme pressure additive(s).

Workpiece corrosion inhibitors are additives used in metal working fluids to reduce the amount of corrosion caused by the presence of water that pools in depressions and imperfections of the workpiece or tool surface. Any workpiece corrosion inhibitors known in the art are suitable provided that they do not interfere with the desired antimicrobial features of the metal working fluid. The corrosion inhibitors may be characterized as cast iron corrosion inhibitors, aluminum corrosion inhibitors, yellow metal corrosion inhibitors, or the like. The type of metal the workpiece if made from will determine the type of corrosion inhibitor or a combination of suitable corrosion inhibitors to be used in the metal working composition. Examples of workpiece corrosion inhibitors are ethanolamine combined with boric acid, triazole compounds such as benzotriazole or tolyltriazole, thiadiazoles, organic carboxylic acids having 6-10 carbon atoms, or dicarboxylic acids having 10-14 carbon atoms, sodium molybdate, sodium metasilicates, sodium borate, or any mixtures thereof. The workpiece corrosion inhibitor(s) may be present in the metal working fluid in an amount of about 0 to 15 wt. %, preferably about 1 to 10 wt. %, most preferably, about 2 to 5 wt. %. The metal working fluid may include about 0 to 15 wt. %, preferably about 1 to 10 wt. % of cast iron corrosion inhibitor, and/or about 0 to 5 wt. %, more preferably about 0.1 to 0.5 wt. % of aluminum corrosion inhibitor, and/or about 0 to 5 wt. %, more preferably about 0.1 to 0.5 wt. % of the yellow metal corrosion inhibitor. The metal working composition may include at least, with increasing preference in the order given, about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7 or 4.8 wt. %, and not more than, with increasing preference in the order given, about 15, 14, 13, 12, 11, 10, 9, 8, 7, 6, or 5 wt. % of the workpiece corrosion inhibitor(s).

Anti-foaming agents are additives used to reduce foaming in aqueous alkaline metal working fluids which may interfere with metal working processes. Foaming is undesirable in metal working operations because it may reduce cooling at the workpiece-tool contact zone and cause numerous containment transport and control problems. Examples of anti-foaming agents include siloxane glycol copolymers, polyether modified polysiloxanes, reaction products of silicon dioxide and organosiloxanes, organosiloxane polymers, hydrophobically treated silica or ethoxylated/propoxylated hydrocarbons, waxes, calcium nitrate, calcium acetate, or mixtures thereof. The amount of anti-foaming agent(s) in the metal working fluid may be about 0.05 to 2 wt. %, more preferably about 0.1 to 0.5 wt. %, most preferably about 0.3 to 0.4 wt. %. The metal working composition may include at least, with increasing preference in the order given, about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, or 0.38 wt. % and not more than, with increasing preference in the order given, about 2.0, 1.9, 1.8, 1.7, 1.6, 1.5, 1.4, 1.3, 1.2, 1.0, 0.9, 0.8, 0.7, 0.6, 0.5, 0.49, 0.48, 0.47, 0.46, 0.45, 0.44, 0.43, 0.42, 0.41, or 0.40 wt. % of anti-foaming agent(s).

The metal working fluid may comprise one or more surfactants useful as emulsifiers and/or hydrotropes. Emulsifiers are surface-active agents that promote the formation and stabilization of the metal working fluid. As used herein, hydrotrope includes materials that solubilize hydrophobic compounds in aqueous solutions and/or act as coupling agents. The metal working fluids may become unstable under varying process conditions. For example, composition of the water, water hardness, temperature, pH, and other variables can vary over wide ranges during the metal working processes. For example, after preparation of the metal working fluid, the ionic strength and/or water hardness may significantly increase during the operation due to evaporation of water or incoming metal fines and ions, resulting in a reduction or loss of relevant properties like emulsion stability, film forming properties, and dispersing capacity. Such instability is undesirable with respect to the metal working fluids. Thus, one or more emulsifiers or hydrotropes may be added to the metal working fluid to maximize solubility of hydrophobic components in the aqueous compositions and emulsion stability under varying operating conditions. The emulsifier and/or hydrotrope may be any suitable ionic surfactant, nonionic surfactant, Gemini emulsifier, or amphotropic surfactant, individually and in the form of mixtures of different surfactants. The emulsifier and/or hydrotrope may be used in pure form or as solutions of one or more emulsifiers and/or hydrotropes in water or organic solvents. Exemplary useful emulsifiers and/or hydrotropes may include alkoxylated fatty alcohols, alkylated polyglycol ethers, alkylated carboxylic acids, sodium sulfonates, fatty acid amides, synthetic sulfonates, nonionic ethoxylates, or the like. The metal working fluid may comprise about 0 to 25 wt. %, more preferably about 1 to 15 wt. %, most preferably about 5 to 10 wt. % of emulsifier(s) and/or hydrotrope(s). The metal working composition may include at least, with increasing preference in the order given, about 0.0, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 wt. %, and not more than, with increasing preference in the order given, about 25, 24, 23, 22, 21, 20, 19, 18, 17, 16, 15, 14.5, 14.0, 13.5, 13.0, 12.5, 12.0, 11.5, 11.0, 10.5, or 10.0 wt. % of emulsifier(s) and/or hydrotrope(s).

Boundary lubricant additives reduce friction and wear by maintaining a physical boundary between contacting surfaces. These additives contain polar groups attracted to the metal or metal oxide at the surface and non-polar groups which are not strongly attracted to the metal or metal oxide and form a slippery layer as they extend away from the surface. The boundary lubricant additives thus provide a thin deformable layer of organic molecules that physically adheres to the surface by molecular attraction of the lubricant to the metal surface. Exemplary boundary lubricant additives used in metal working fluids are often natural products and may be based on fatty amides, fatty acids, animal fatty oils, vegetable fatty oils, partial esters, polymeric esters, oleyl alcohol, or the like. The metal working fluid may comprise about 0 to 40 wt. %, more preferably about 2 to 13 wt. %, most preferably, about 3 to 5 wt. % of boundary lubricant additive(s). The metal working composition may include at least, with increasing preference in the order given, about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7 or 4.8 wt. % and not more than, with increasing preference in the order given, about 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 wt. % of boundary lubricant additive(s).

Hydrodynamic lubricant additives are used to enhance friction reduction of the metal working fluid. Hydrodynamic lubricant additives separate surfaces sliding over each other with a coherent lubricating film or liquid. The non-compressible nature of the film separates the surfaces to prevent metal to metal contact completely. Hydrodynamic lubricant additives may be various mineral oils, such as petroleum fractionation products; desirably naphthenic oils, such as by way of non-limiting example, a hydrotreated heavy naphthenic distillate. The amount of the hydrodynamic lubricant additive(s) may be about 0 to 50 wt. %, more preferably about 5 to 30 wt. %, even more preferably about 10 to 20 wt. %. The metal working composition may include at least, with increasing preference in the order given, about 0.0, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, or 19.5 wt. %, and not more than, with increasing preference in the order given, about 50, 48, 46, 44, 42, 40, 38, 36, 34, 32, 30, 29, 28, 27, 26, 25, 24, 23, 22, 21 or 20 wt. % of hydrodynamic lubricant additive(s).

The pH buffers may be utilized to keep pH of the metal working fluids at a nearly constant value. Exemplary pH buffer solutions may include alkanolamines, alkali metal hydroxides such as NaOH and KOH, carboxylic acids, or the like. Preferably, the pH buffers are free of boric acid or derivatives thereof. The metal working fluid may comprise about 0.2 to 20 wt. %, more preferably about 1 to 8 wt. %, most preferably 2 to 3 wt. % of carboxylic acid buffer(s) and about 0 to 25 wt. %, more preferably about 2 to 15 wt. %, most preferably about 2.5 to 7 wt. % of organic amine buffer component(s). The metal working composition may include at least, with increasing preference in the order given, about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 6.0, 6.1, 6.2, 6.3, 6.4, 6.5, 6.6, 6.7, 6.8, 6.9, 7.0, and not more than, with increasing preference in the order given, about 20, 19, 18, 17, 16, 15, 14, 13, 12, 11, 10, 9.5, 9, 8.5, 8 or 7.5 wt. % of pH buffer(s).

The pH of the metal working fluid may be, in increasing order of preference, about 8.5, 8.6, 8.7, 8.8, 8.9, 9.0, 9.1, 9.2, 9.3, 9.4, 9.5, 9.6, 9.7, 9.8, 9.9 or more, and less than, in increasing order of preference, about 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9 or 12. The pH of the metal working fluid may be about 8.5 to 12.0, more preferably about 8.8 to 11.0, even more preferably about 9.0 to 10.0, and most preferably about 9.3 to 9.6.

Biocides provide protection against micro-organisms in aqueous metal working fluids, inhibiting both bacterial and fungal growth. Biocides may be bactericides, fungicides, or so called broad spectrum biocides. Numerous biocides have been developed. Exemplary biocides may include triazine compounds, nitromorpholine, sodium omadine, sodium pyrithione, bromonitriles, phenols, halogen substituted carbamates, isothiazolone derivatives, or the like. Preferably, the biocides used does not present health hazards to humans. The metal working fluid may comprise about 0.05 to 2 wt. % of a biocide(s). Preferably, the amount of biocide(s) is about 0.1 to 0.5 wt. %, even more preferably about 0.2 to 0.3 wt. %. The metal working composition may include at least, with increasing preference in the order given, about 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47 or 0.48 wt. % and not more than, with increasing preference in the order given, about 2.0, 1.95, 1.90, 1.85, 1.80, 1.75, 1.70, 1.65, 1.60, 1.55, 1.50, 1.45, 1.40, 1.35, 1.30, 1.25, 1.20, 1.15, 1.00, 0.95, 0.90, 0.85, 0.80, 0.75, 0.7, 0.65, 0.60, 0.55, or 0.50 wt. % of biocide(s).

The esters, fatty acids, and oils in metal working fluids form films on the surfaces of tools and work pieces that they contact during metal working operations. The films are typically formed when the polarities of the esters, fatty acids, and oils associate with the charges on the metal surfaces. Any film forming additive is suitable so long as it does not interfere with the stability, reusability, or antimicrobial action of the metal working fluid. Mineral oils form a hydrodynamic boundary between the tool and work piece. This film acts as a boundary to lubricate the tool and the work piece contact zone.

Anti-mist agents reduce suppress mist formation in the metal working fluids. Exemplary anti-mist agents which may be utilized in the metal working fluid include polyisobutenes, polyacrylates, polyethylene oxide, and other natural and synthetic polymers. The film-forming additive(s), anti-mist agent(s), humectant(s), thickener(s), chelating agent(s), dye(s), and other additive(s) may be present in any suitable amount provided that their use does not interfere with the desired antimicrobial action.

The metal working fluid comprises water in an amount of up to 99.5 wt. %. The amount of water may be, for example, about 40 to 99.5 wt. %, about 50 to 99 wt. %, about 60 to 89 wt. %, about 70 to 85 wt. %. The metal working composition may include at least, with increasing preference in the order given, about 40, 42, 44, 46, 48, 50, 52, 54, 56, 58, 60, 62, 64, 66, 68, 70, 72, 74, 76, 78, 80, 81, 82, 83, or 84 wt. %, and not more than, with increasing preference in the order given, about 99.5, 99.4, 99.3, 99.2, 99.1, 99.0, 89.9, 89.8, 89.7, 89.6, 89.5, 89.4, 89.3, 89.2, 89.1, 89, 88.5, 88.0, 87.5, 87.0, 86.5, 86.0, 85.5 or 85.0 wt. % of water.

The invention is further directed to a metal working composition concentrate including at least one amine of Formulas Ia, Ib, or Ic which may exceed about 15 wt. %, based on the total weight of the metal working fluid. In the absence of water, the metal working composition concentrate may be characterized as an oil-containing, water-emulsifiable lubricant. The amounts of amine and other components in the concentrate depend on the dilution factor necessary to convert the concentrates into aqueous alkaline metal working fluids. The concentrations of the amines of formulae Ia, Ib, and/or Ic in the concentrate are preferably adjusted based on the desired degree of dilution.

The aqueous alkaline metal working fluids are subject to normal degradation over time such as from contact with local aqueous diluents, exposure to light, or exposure to air. In addition, the metal working fluids are often exposed to extreme stresses such as elevated pressure or temperature, especially in the workpiece-tool contact zone which may assist in the degradation of the fluid components. As a consequence, aqueous alkaline metal working fluids have a finite lifetime in use and are replaced. Typically, the replacement occurs by incrementally removing a small portion of the metal working fluid from service and replacing the removed portion with an equivalent amount of virgin metal working fluid. The aqueous alkaline metal working fluids of the present disclosure behave similarly and typically have comparable lifetimes to analogous working fluids that do not contain the at least one amine of formula Ia, Ib, or Ic.

The disclosure is further directed to processes for inhibiting microbial growth in aqueous alkaline metal working fluids and/or in aqueous alkaline metal working environments. The processes comprise the incorporation of a *Mycobacterium* inhibitory effective amount of at least one amine of the above formulas Ia, Ib, or Ic, wherein the amine may be a primary amine or a tertiary amine. The primary amine may be mono- or di-primary amine. The primary amine in Formulas Ia and Ib may be linear, branched, or cyclic. The primary amine is aliphatic. $R_1$ in Formula Ia is independently $C_2$-$C_{18}$ alkyl or $C_4$-$C_{16}$ alkyl. Alternatively, $R_1$ is independently $C_5$-$C_{12}$ alkyl. Preferably, at least one $R_1$ is $C_6$-$C_8$ alkyl. $R_2$ in Formula Ib is independently $C_5$-$C_8$ alkyl or C6 cycloalkylene. Preferably, at least one $R_2$ is $C_7$-$C_8$ alkyl or cyclohexane. The tertiary amine in Formula Ic includes primary amine end groups. Even more preferably, the amine of Formula Ia is dimethylhexylamine, 2-ethylhexylamine, heptylamine, or octylamine. Even more preferably, the amine of Formula Ib is 2-methylpentane-1,5-diamine or 1,4-cyclohexanediamine. The amine of formula Ic is tris(2-aminoethyl)amine. The amine is free of ether groups.

The "inhibitory effective amount" refers to an amount of at least one amine that may prevent, inhibit, or reduce the rate of *Mycobacterium* growth relative to its growth in the absence of the at least one amine compound in the aqueous alkaline metal working fluid or a metal working environment. Typical levels of amine in the aqueous alkaline metal working fluid include but are not limited to from about 0.2 to 15 wt. %, based on the total weight of the metal working fluid.

Typically, a metal working environment includes any airspace, liquid or solid surface on or in a reasonable proximity to the workpiece being modified, the tool modifying the workpiece or the sumps, pumps, reservoirs or other equipment used to move or circulate the metal working fluid at the location where the metal working is taking place. Notably, such environments include those occupied by workers operating metal working machinery who may come into contact with microbiological agents such as *Mycobacterium*.

Other than in the operating examples, or where otherwise indicated, all numbers expressing quantities of ingredients, reaction conditions, or defining ingredient parameters used herein are to be understood as modified in all instances by the term "about." Throughout the description, unless expressly stated to the contrary: percent, "parts of," and ratio values are by weight or mass; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description or of generation in situ within the composition by chemical reaction(s) between one or more newly added constituents and one or more constituents already present in the composition when the other constituents are added; specification of constituents in ionic form additionally implies the presence of sufficient counterions to produce electrical neutrality for the composition as a whole and for any substance added to the composition; any counterions thus implicitly specified preferably are selected from among other constituents explicitly specified in ionic form, to the extent possible; otherwise, such counterions may be freely selected, except for avoiding counterions that act adversely to an object of the invention; molecular weight (MW) is weight average molecular weight; the word "mole" means "gram mole," and the word itself and all of its grammatical variations may be used for any chemical species defined by all of the types and numbers of atoms present in it, irrespective of whether the species is ionic, neutral, unstable, hypothetical, or in fact a stable neutral substance with well-defined molecules; and the term "storage stable" is to be understood as including dispersions that show no visually detectable tendency toward phase separation as well as those that show hard water precipitates of calcium and magnesium, but no water oil phase separation over a period of observation of at least 72, 96, 120, 150, 200, 250, 300, 320, or preferably at least 336, hours during which the material is mechanically undisturbed and the temperature of the material is maintained at ambient room temperatures (18 to 25° C.).

For a variety of reasons, it is preferred that metal working fluids according to the invention may be substantially free from many ingredients used in compositions for similar purposes in the prior art. Specifically, it is increasingly preferred in the order given, independently for each preferably minimized ingredient listed below, that aqueous compositions according to the invention, when directly contacted with metal in a process according to this invention, contain no more than 1.0, 0.5, 0.35, 0.10, 0.08, 0.04, 0.02, 0.01, 0.001, or 0.0002 percent, more preferably said numerical values in grams per liter, of each of the following constituents: boron, including but not limited to boric acid and salts thereof; cadmium; nickel; cobalt; inorganic fluorides, chlorides and bromides; tin; copper; barium; lead; chromium; adipic acid and salts thereof; nitrogen-based acids and their salts, e.g. nitrates and nitrites; sulfur-based acids and their salts, e.g. sulfates and sulfites.

As employed above and throughout the disclosure, the following terms, unless otherwise indicated, shall be understood to have the following meanings.

"Alkyl" refers to an optionally substituted, saturated straight, branched, or cyclic hydrocarbon having from about 1 to about 20 carbon atoms (and all combinations and subcombinations of ranges and specific numbers of carbon atoms therein which do not adversely affect ether amine solubility in the metal working fluid or metal working fluid performance. Preferably, the alkyl is a straight chain hydrocarbon. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, 3-methylpentyl, 2,2-dimethylbutyl, and 2,3-dimethylbutyl, 2-ethylhexyl, octyl, decyl, undecyl, dodecyl, tridecyl, tetradecyl, pentadecyl, hexadecyl, heptadecyl, octadecyl, nonadecyl, and eicosyl.

"Alkylene" refers to a bivalent alkyl radical having the general formula $—(CH_2)_n—$, where n is 2 to 10. Non-limiting examples include methylene, trimethylene, pentamethylene, and hexamethylene. Alkylene groups can be substituted or unsubstituted. In some embodiments, n is preferably 2 to 4. In some more preferable embodiments, n is 3. In other embodiments, the alkylene moiety has one or more alkyl branches. In these embodiments the sum of the number of carbon atoms in the alkylene and alkyl branches is an integer in the range of 2 to 10.

EXAMPLES

*Mycobacterium* species are generally considered more similar to Gram-negative bacteria than Gram-positive bacteria based on conserved gene content. Other analysis has shown that *Mycobacterium* tuberculosis shares relatively more orthologous genes for energy production and conversion with Gram-negative bacteria, in particular, *Escherichia coli* and *Pseudomonas aeruginosa*, than with Gram-positive bacteria. As such, initial screening of candidate biostats was performed with a mixed Gram-negative bacteria-containing inoculant, rather than the slower growing and more resistant *Mycobacterium* species on the basis that those biostat candidates that were ineffective against Gram-negative bacteria were unlikely to be effective against *Mycobacterium*.

Biostat Candidate Screening

Minimum Inhibitory Concentration Testing (MIC)

An inoculation broth for determining the minimum inhibitory concentration of candidate biostats was prepared as is known in the microbiological industry using a conventional aqueous semi-synthetic metal working fluid that had been used in a metal working environment and had tested positive for the presence of Gram-negative bacteria as the bacterial source. The metal working fluid was first cultured to increase concentration of bacteria, forming an inoculum. The inoculum was then used, as described below, to perform minimum inhibitory concentration testing on metal working fluid solution samples containing the candidate biostats to assess the inhibitory effect of the alkylamines for metal working fluid.

The Intermediate

A metal working fluid was prepared according to the Table I below:

TABLE I

| The Intermediate: | | |
|---|---|---|
| Component Name | Component Function | Amount [wt. %] |
| Deionized water | Solvent | 47.15 |
| Monoethanolamine | pH buffer | 8.50 |
| Fatty alcohol alkoxylate based on oleyl-/cetyl alcohol | Emulsifier/hydrotrope | 6.25 |
| Isononanoic acid | pH buffer | 3.50 |
| Sodium pyrithione | Biocide | 0.25 |
| Tolyltriazole, Na 50% | Corrosion inhibitor | 0.25 |
| Alkyl ether carboxylic acid | Emulsifier/hydrotrope | 3.00 |
| Silicone defoamer | Anti-foaming agent | 0.20 |
| Mineral oil | Film-forming additive | 20.00 |
| Alkanolamide | Boundary lubricant additive | 1.00 |
| Phosphate ester | Extreme pressure additive | 2.00 |
| Organic diacid mixture having $C_{12}$-$C_{16}$ dicarboxylic acid | Corrosion inhibitor | 4.90 |
| Total | | 97.00 |

Amounts are given in weight percent after addition of amine-based biostats into the Intermediate in the amount of 3 wt. % for Examples 1-7 and Comparative Examples C1-C14, below.

Examples 1-7 and Comparative Examples C1-C14

Examples 1-7 and Comparative Examples C1-C14 were prepared by adding amine-based biostats into the Intermediate in the amount of 3 wt. %, based on the total weight of the metal working fluid. Formulae of the amine-based biostats added into the Examples 1-7 and Comparative Examples C1-C14 are recited in Table II.

TABLE II

Amine-based biostats of Examples 1-7 and Comparative Examples C1-C14

| Example/ Comparative Example No. | Chemical Name | IUPAC nomenclature | Molecular Formula |
|---|---|---|---|
| 1 | 1,5-dimethylhexylamine | 6-methylheptan-2-amine | $C_8H_{19}N$ |
| 2 | 2-ethylhexylamine | 2-ethylhexan-1-amine | $C_8H_{19}N$ |
| 3 | Heptylamine | Heptan-1-amine | $C_7H_{17}N$ |
| 4 | 1,4-cyclohexanediamine | Cyclohexane-1,4-diamine | $C_6H_{14}N_2$ |
| 5 | Methylpentamethylene diamine | 2-methylpentane-1,5-diamine | $C_6H_{16}N_2$ |
| 6 | Octylamine | Octan-1-amine | $C_8H_{19}N$ |
| 7 | Tris(2-aminoethyl)amine | N',N'-bis(2-aminoethyl)ethane-1,2-diamine | $C_6H_{18}N_4$ |
| C1 | 1,6-diaminohexane | Hexane-1,6-diamine | $C_6H_{16}N_2$ |
| C2 | 1,3-bis(aminomethyl) cyclohexane | [3-(aminomethyl)cyclohexyl]methanamine | $C_8H_{18}N_2$ |
| C3 | 1,2-cyclohexanediamine | Cyclohexane-1,2-diamine | $C_6H_{14}N_2$ |
| C4 | Amylamine | Pentan-1-amine | $C_5H_{13}N$ |
| C5 | 2-methylcyclohexylamine | 2-methylcyclohexan-1-amine | $C_7H_{15}N$ |
| C6 | N-ethylcyclohexylamine | N-ethylcyclohexanamine | $C_8H_{17}N$ |
| C7 | Cyclohexylamine | Cyclohexanamine | $C_6H_{13}N$ |
| C8 | Aminomethylcyclohexane | Cyclohexylmethanamine | $C_7H_{15}N$ |
| C9 | Tris(2-ethylhexylamine) | 2-ethyl-N,N-bis(2-ethylhexyl)hexan-1-amine | $C_{24}H_{51}N$ |
| C10 | 1,3-pentanediamine | Pentane-1,3-diamine | $C_5H_{14}N_2$ |
| C11 | 4,4'-methylene bis(cyclohexylamine) | 4-[(4-aminocyclohexyl)methyl]cyclohexan-1-amine | $C_{13}H_{26}N_2$ |
| C12 | N,N,N',N'-tetramethyl-1,6-diaminohexane | N,N,N',N'-tetramethylhexane-1,6-diamine | $C_{10}H_{24}N_2$ |
| C13 | N,N,N',N'',N''-pentamethyl-dipropylenetriamine | N'-[3-(dimethylamino)propyl]-N,N,N'-trimethylpropane-1,3-diamine | $C_{11}H_{27}N_3$ |
| C14 | Pentamethyldiethylene triamine | N'-[2-(dimethylamino)ethyl]-N,N,N'-trimethylethane-1,2-diamine | $C_9H_{23}N_3$ |

The resulting metal working fluids with the amine-based biocides were clear, stable products which did not require any further adjustments. In comparison with the metal working compositions disclosed in U.S. Pat. No. 7,595,288, which include both amine and ether functional groups, Examples 1-7 and Comparative Examples C1-C4 were easier to formulate into a water-based product. Additionally, no objectionable odor was present in Examples 1-7 and Comparative Examples C1-C14.

Each of the Examples 1-7 and Comparative Examples C1-C14 was adjusted with isononanoic acid or monoethanolamine to a pH of 9.3-9.6. The Examples and Comparative Examples were each made into three samples of tap water dilutions of the metal working fluid at different concentrations: at 3, 4, or 5 w/w % or 4, 5, or 6 w/w %. Each dilution was then inoculated with the inoculation broth so that the final concentration of bacteria in the sample was about $10^5$/ml. An aqueous dilution of a commercially available metal working fluid containing dicyclohexylamine (DCHA) was used as a standard and was tested at the same concentrations of metal working fluid with no pH adjustment needed to achieve a pH of 9.3-9.6.

The testing was conducted in two separate Phases: Examples 1-5 and Comparative Example C1-C8 were tested in Phase 1, and Examples 6 and 7 and Comparative Examples C9-C14 were tested in Phase 2. In both Phase 1 and 2, dip slide measurements were taken after 24 and 48 hours of slide incubation at 37.78° C. (100° F.). A slide measurement at each chosen concentration and elapsed time period constituted one "test value."

In Phase 1, all Examples and Comparative Examples were tested three times to ensure repeatability. Bacterial counts at 24 and 48 hours were measured and converted to log values, and a "differential value" was calculated versus the DCHA-containing standard reference data. The test results for Examples 1-5 and Comparative Example C1-C8 are in Table III below. In the Table III below, values between 0 and 6 were given to illustrate biostatic efficacy concerning Gram-negative bacteria of each example in each round. Numeral 3 indicates that the example exactly matched the DCHA standard. A value higher than 3 indicates that the example surpassed the DCHA standard. Values lower than 3 indicate that the example provided lower biostatic efficacy than the DCHA standard.

TABLE III

Phase 1 Test results for Examples 1-5 and Comparative Examples C1-C8

| Example No. | Differential Value Scores | | | |
|---|---|---|---|---|
| | Round 1 | Round 2 | Round 3 | Average |
| 1 | 4.5 | 4 | 4.5 | 4.3 |
| 2 | 4 | 4.5 | 4.5 | 4.3 |
| 3 | 4 | 4 | 4.5 | 4.2 |
| 4 | 4 | 4.5 | 2.5 | 3.7 |
| 5 | 2.5 | 4.5 | 3 | 3.3 |
| C1 | 2 | 4 | 1.5 | 2.5 |
| C3 | 2 | 4 | 1 | 2.3 |
| C2 | 2.5 | 4 | 1 | 2.5 |
| C6 | 1.5 | 2.5 | 1 | 1.7 |
| C4 | 1.5 | 2.5 | 1 | 1.7 |
| C7 | 1 | 2.5 | 1 | 1.5 |
| C8 | 1 | 2.5 | 1 | 1.5 |
| C5 | 1 | 2.5 | 1.5 | 1.7 |

As is apparent from Table III, Examples 1-5 surpassed the DCHA standard. Comparative Examples C1-C8 exhibited lower biostatic capacity than the DCHA standard with respect to Gram-negative bacteria.

In Phase 2, Examples 6 and 7 and Comparative Examples 9-14 were tested in a similar fashion to testing in Phase 1, but only two rounds of testing for each Example and Comparative Example and concentration were performed. The test results for Examples 6 and 7 and Comparative Examples 9-14 are listed below in Table IV. Results of bacterial counts reflecting the amount of new Gram-negative bacteria colonies at 24 and 48 hours are shown for Round 1 and Round 2 for 3, 4, 5, and 6 w/w %. 0 indicates no bacterial growth.

TABLE IV

Phase 2 Test results for Examples 6 and 7 and Comparative Examples 9-14

| Example No. | Dilution [%] | Round 1 Amount of new Gram-negative bacteria colonies | | Round 2 Amount of new Gram-negative bacteria colonies | |
|---|---|---|---|---|---|
| | | 24 hours | 48 hours | 24 hours | 48 hours |
| DCHA standard | 3 | 0 | 0 | — | — |
| | 4 | 0 | $10^2$ | $10^2$ | $10^7$ |
| | 5 | 0 | 0 | 0 | $10^5$ |
| | 6 | — | — | 0 | $10^3$ |
| 6 | 3 | 0 | 0 | — | — |
| | 4 | 0 | 0 | 0 | 0 |
| | 5 | 0 | 0 | 0 | 0 |
| | 6 | — | — | 0 | 0 |
| 7 | 3 | 0 | $10^3$ | — | — |
| | 4 | 0 | 0 | 0 | $10^2$ |
| | 5 | 0 | 0 | 0 | $10^2$ |
| | 6 | — | — | 0 | $10^2$ |
| C10 | 3 | $10^7$ | $10^7$ | — | — |
| | 4 | $10^5$ | $10^7$ | $10^2$ | $10^7$ |
| | 5 | $10^3$ | $10^7$ | $10^2$ | $10^7$ |
| | 6 | — | — | $10^2$ | $10^7$ |
| C12 | 3 | $10^5$ | $10^7$ | — | — |
| | 4 | $10^5$ | $10^7$ | $10^2$ | $10^7$ |
| | 5 | $10^5$ | $10^7$ | $10^2$ | $10^7$ |
| | 6 | — | — | $10^2$ | $10^7$ |
| C9 | 3 | $10^7$ | $10^7$ | — | — |
| | 4 | $10^5$ | $10^7$ | $10^3$ | $10^7$ |
| | 5 | $10^4$ | $10^7$ | $10^2$ | $10^7$ |
| | 6 | — | — | $10^2$ | $10^7$ |
| C11 | 3 | $10^7$ | $10^7$ | — | — |
| | 4 | $10^5$ | $10^7$ | $10^2$ | $10^7$ |
| | 5 | $10^5$ | $10^7$ | $10^2$ | $10^7$ |
| | 6 | — | — | $10^2$ | $10^7$ |
| C13 | 3 | $10^7$ | $10^7$ | — | — |
| | 4 | $10^7$ | $10^7$ | $10^2$ | $10^7$ |
| | 5 | $10^3$ | $10^7$ | $10^2$ | $10^7$ |
| | 6 | — | — | $10^2$ | $10^7$ |
| C14 | 3 | $10^7$ | $10^7$ | — | — |
| | 4 | $10^7$ | $10^7$ | $10^3$ | $10^7$ |
| | 5 | $10^7$ | $10^7$ | $10^2$ | $10^7$ |
| | 6 | — | — | $10^3$ | $10^7$ |

As is apparent from Table IV, Examples 6 and 7 showed lesser number of colonies over time as compared to the DCHA control. In Phase 2, Examples 6 and 7 thus surpassed the DCHA standard with respect to biostatic efficacy regarding Gram-negative bacteria while Comparative Example 9-14 demonstrated worse biostatic efficacy than the DCHA control.

It has thus been surprisingly and unexpectedly discovered that various amines of relatively similar structures and molecular sizes disclosed herein exhibit different biostatic properties with respect to Gram-negative bacteria in the metal working fluids.

For example, Examples 3 and 6 containing heptylamine and octylamine, respectively, showed better biostatic performance than the DCHA control while Comparative Example C4 containing structurally similar pentylamine exhibited worse biostatic capabilities than the DCHA control. Similarly, Example 4 containing 1,4-cyclohexanediamine showed better biostatic performance than the DCHA standard. In contrast, Comparative Example 3 containing structurally similar amine, 1,2-cyclohexanediamine performed below the DCHA standard.

*Mycobacterium* Challenge

Example 5 outperformed DCHA, by the closest margin of the Examples according to the invention. As the candidate with similar but improved performance over DCHA in the screening tests, Example 5 was selected for testing of its biostatic effectiveness against *Mycobacteria* inoculated metal working fluid.

A sample metal working fluid was prepared incorporating the amine-based biostat of Example 5, as shown in Table V below.

TABLE V

Metal working fluid including biostat of Example 5

| Component Name | Component Function | Amount [wt. %] |
|---|---|---|
| Example 5 | Biostat | 3.00 |
| Ethanolamines | Amine pH buffer component | 8.50 |
| Alkyl polyglycol ether | Emulsifier/hydrotrope | 1.50 |
| Isononanoic acid | Acid pH buffer component | 0.50 |
| 2-Pyridinethiol, 1-oxide, sodium salt solution | Biocide | 0.25 |
| 1H-Benzotriazole, (4 or 5)-methyl, sodium salt solution | Yellow metal corrosion inhibitor | 0.25 |
| Alkyl ether carboxylic acid | Emulsifier/hydrotrope | 2.00 |
| Tall oil, fatty acid | Emulsifier/hydrotrope | 1.60 |
| Polyoxyalkylene polymer and 2,4,7,9-tetramethyl-5 decyne-4,7-diol | Defoamer | 0.20 |
| Deionized water | Carrier | 48.55 |
| Oleyl/cetylalcohol | Boundary lubricant additive | 1.00 |
| Alkoxylated fatty alcohol | Emulsifier/hydrotrope | 1.25 |
| Naphthenic petroleum distillate | Hydrodynamic lubricant additive | 20.00 |
| Proprietary alkanolamide | Boundary lubricant additive | 1.00 |
| Phosphate ester | Extreme pressure lubricant additive | 2.00 |
| Ethoxylated fatty alcohols | Emulsifier/hydrotrope | 3.50 |
| Organic diacid mixture, C12-C16 | Cast iron corrosion inhibitor | 4.90 |

A tap water dilution of the metal working fluid for the *Mycobacterium* challenge was made to a concentration of 5 w/w %. The sample was tested by Biosan Laboratories, in Warren, Mich., USA, an independent commercial biological laboratory, for biostatic activity against *Mycobacterium* and against mixed Gram-negative bacteria.

The test method evaluated the effectiveness of antimicrobial agents in controlling *Mycobacterium* immunogenum in the presence of high background population of Gram-negative and other bacteria responsible for metal working fluid deterioration. Sample metal working fluids including the biostat of Example 5 and antimicrobial agents were prepared at use concentrations. 1% iron chips were added to the diluted metal working fluid samples. Two microbial populations were then introduced at a 1% level: an undefined Gram-negative bacterial inoculum isolated from a contaminated metal working fluid, and an inoculum containing *Mycobacterium* immunogenum. The inoculated test metal working fluids were incubated at room temperature (22+2° C.) on an orbital shaker for four weeks. During the four week test period, the metal working fluids were evaluated twice weekly for bacterial and mycobacterial contamination before being re-inoculated with both microbial suspensions at 1% concentrations. This re-inoculation method ensured sufficient viable Gram-negative and *Mycobacterium* levels throughout the test. The test results are shown in the Table VI below.

TABLE VI

Biostatic efficacy of Example 5 in the metal working fluid measured over a period of four weeks and is shown below.

| | | Mixed Gram Negative Bacteria [cfu/ml] | | | *Mycobacterium immunogenum* [cfu/ml] | | |
|---|---|---|---|---|---|---|---|
| Week | Day | Inoculum | Sample 1 | Sample 2 | Inoculum | Sample 1 | Sample 2 |
| 1 | 0 (Initial Inoculum) | $>1 \times 10^8$ | $\sim 1 \times 10^6$ | $\sim 1 \times 10^6$ | $1 \times 10^7$ | $\sim 1 \times 10^5$ | $\sim 1 \times 10^5$ |
|   | 2 | $>1 \times 10^8$ | <2 | <2 | $2 \times 10^6$ | <2 | <2 |
| 2 | 7 | $>1 \times 10^8$ | <2 | <2 | $1 \times 10^6$ | <2 | <2 |
|   | 9 | $>1 \times 10^8$ | <2 | <2 | $1 \times 10^6$ | <2 | <2 |
| 3 | 14 | $>1 \times 10^8$ | <2 | <2 | $1 \times 10^7$ | <2 | <2 |
|   | 16 | $>1 \times 10^8$ | <2 | <2 | $1 \times 10^6$ | <2 | <2 |
| 4 | 21 | $>1 \times 10^8$ | <2 | <2 | $1 \times 10^5$ | <2 | <2 |
|   | 23 | N/A | <2 | <2 | N/A | <2 | <2 |

Table VI illustrates the very low growth, essentially no growth of *Mycobacterium* and Gram-negative bacteria in the presence of a biostat according to the invention in the metal working fluid, over the entire 4 week period.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus, it is understood that the formulas used herein, as well as the chemical names attributed to the correspondingly indicated compounds, are not intended to limit the invention in any way.

As required, detailed embodiments of the present invention are disclosed herein; however, it is to be understood that the disclosed embodiments are merely exemplary of the invention that may be embodied in various and alternative forms. Therefore, specific structural and functional details disclosed herein are not to be interpreted as limiting, but merely as a representative basis for teaching one skilled in the art to variously employ the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A process for shaping a metal workpiece comprising:
contacting a metal workpiece with a metal working tool in the presence of an aqueous metal working fluid comprising at least one amine of Formula (Ia) or (Ic):

(Ia)

wherein each $R_1$ is independently $C_5$-$C_{10}$ alkyl, or $(NH_2CH_2CH_2)_3N$,    Formula Ic present in an effective *Mycobacterium* inhibiting amount of about 0.5 wt. % to 15 wt. % of the at least one amine, based on the total weight of the aqueous metal working fluid, with the proviso that the at least one amine is not pentylamine;
wherein the aqueous metal working fluid is free of amines comprising an ether group; and
wherein the aqueous metal working fluid has an alkaline pH and further comprises at least one workpiece corrosion inhibitor; and at least one extreme pressure additive selected from phosphate esters, polysulfides, chlorinated additives and combinations thereof.

2. The process of claim 1, wherein the aqueous metal working fluid comprises about 1 to 7 wt. % of the at least one amine, based on the total weight of the aqueous metal working fluid.

3. The process of claim 1, wherein the aqueous metal working fluid remains effective against growth of *Mycobacterium* after exposure to a workpiece-tool contact zone working pressure of greater than about 60 psi.

4. The process of claim 1, wherein the at least one corrosion inhibitor comprises organic carboxylic acid having 12-16 carbon atoms, benzotriazole, sodium salt of tolyltriazole, or a combination thereof.

5. The process of claim 1, wherein the at least one pH buffer comprises an organic amine, a carboxylic acid, or a mixture thereof.

6. The process of claim 1, wherein the aqueous metal working fluid is triazine-free, dicyclohexylamine-free, and/or boron-free.

7. The process of claim 1, wherein the aqueous metal working fluid further comprises water, at least one pH buffer, a biocide, an emulsifier, an anti-foaming agent, or a combination thereof; and the aqueous metal working fluid comprises 40.0 wt. % up to 99.5 wt. % water, based on the total weight of the aqueous metal working fluid.

8. The process of claim 1, wherein the $C_5$-$C_{10}$ alkyl in Formula Ia comprises dimethylhexyl, ethylhexyl, heptyl, or octyl.

9. The process of claim 1, wherein the aqueous metal working fluid comprises at least one of about 0.05 to 2 wt. % of biocide(s), about 0.05 to 2 wt. % of anti-foaming agent(s), about 0.2 to 20 wt. % of pH buffer(s), or a combination thereof, based on the total weight of the aqueous metal working fluid.

10. The process of claim 1, wherein each $R_1$ is independently $C_6$-$C_8$ alkyl.

11. The process of claim 1 further comprising about 0.2 to 15 wt. % of 1,4-cyclohexane diamine and/or 2-methylpentane-1,5-diamine, based on the total weight of the aqueous metal working fluid.

12. A process for reducing the concentration of *Mycobacterium* in an aqueous alkaline metal working environment, comprising:
providing to the metal working environment an aqueous metal working fluid incorporating an effective *Mycobacterium* inhibiting amount of about 1.0 wt. % to 15 wt. % of at least one amine of Formula (Ia) or (Ic), and optionally (Ib), based on the total weight of the aqueous metal working fluid:

(Ia)

wherein each $R_1$ is independently $C_5$-$C_{10}$ alkyl, or $(NH_2CH_2CH_2)_3N$,    Formula Ic:

and optionally further comprising an amine of Formula (Ib):

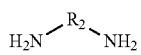
(Ib)

wherein $R_2$ is independently a linear or branched $C_5$-$C_8$ alkyl or $C_6$ cycloalkylene;
with the proviso that the at least one amine is not pentylamine, 1,2-cyclohexanediamine, 1,6-diaminohexane, or 1,3-pentanediamine;
wherein the aqueous metal working fluid is free of amines comprising an ether group;
wherein the aqueous metal working fluid further comprises at least one extreme pressure additive selected from phosphate esters, polysulfides, chlorinated additives and combinations thereof; and
wherein the aqueous metal working fluid has an alkaline pH.

13. The process of claim 12, wherein the at least one amine is selected from 1,5-dimethylhexylamine; 2-ethylhexylamine; heptylamine; octylamine; tris(2-aminoethyl)amine and combinations thereof and optionally further comprises 1,4-cyclohexanediamine and/or 2-methylpentane-1,5-diamine.

14. The process of claim 12, wherein the aqueous alkaline metal working fluid comprises about 1-7 wt. % of the at least one amine, based on the total weight of the aqueous alkaline metal working fluid.

15. The process of claim 12, wherein the aqueous alkaline metal working fluid is free of one or more of: triazine, dicyclohexylamine, boron and combinations thereof.

16. The process of claim 12, wherein the aqueous alkaline metal working fluid is prepared from an oil-containing, water-emulsifiable lubricant concentrate comprising more than about 15 wt. % of the at least one amine, based on the total weight of the aqueous alkaline metal working fluid.

17. An aqueous metal working fluid having an alkaline pH and comprising at least one *Mycobacterium*-inhibitory amine of Formula Ia, Ib or Ic:

wherein each $R_1$ is independently $C_5$-$C_{10}$ branched alkyl, $C_7$ linear alkyl, $C_9$-$C_{10}$ linear alkyl, or

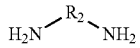

wherein $R_2$ is independently a branched $C_7$-$C_8$ alkyl or a $C_6$ cycloalkylene having the $NH_2$ groups at ring positions 1 and 4, or $(NH_2CH_2CH_2)_3N$,   Formula Ic:

with the proviso that the at least one amine is not a secondary amine, pentylamine, 1,2-cyclohexanediamine, 1,6-diaminohexane, or 1,3-pentanediamine; wherein the aqueous metal working fluid is free of amines comprising an ether group; and wherein a content of the *Mycobacterium*-inhibitory amine in the aqueous metal working fluid is about 2.0 wt. % to 10 wt. %, based on the total weight of the aqueous metal working fluid; and wherein the aqueous metal working fluid further comprises 0.1 to 10 wt. % of at least one extreme pressure additive selected from the group consisting of phosphate esters, polysulfides, chlorinated additives and combinations thereof, wherein the aqueous metal working fluid comprises 40 to 89.9 wt. % water.

18. The aqueous metal working fluid of claim 17, wherein each $R_1$ is independently $C_6$-$C_8$ branched alkyl.

19. The aqueous metal working fluid of claim 17, further comprising 99.5 to 74 wt. % water, and one or more of at least one pH buffer free of boric acid or derivatives thereof, a biocide, an anti-foaming agent, and optionally a corrosion inhibitor, an emulsifier, or a lubricant additive.

20. The aqueous metal working fluid of claim 17, wherein the metal working fluid is free of one or more of: triazine, dicyclohexylamine, boron and combinations thereof.

21. The aqueous metal working fluid of claim 17, further comprising:
a) 0.2 to 20 wt. % of acid-based pH buffer(s); and
b) a non-zero amount up to 25 wt. % of organic amine pH buffer;
c) about 1 to 15 wt. % of emulsifier(s) and/or hydrotrope(s);
d) about 0.05 to 2 wt. % of a biocide;
e) at least one corrosion inhibitor that comprises organic carboxylic acid having 12-16 carbon atoms, benzotriazole, sodium salt of tolyltriazole, or a combination thereof;
f) about 5 to 30 wt. % of hydrodynamic lubricant;
g) about 1 to 5 wt. % of the at least one extreme pressure additive(s); and
h) 2 to 13 wt. % boundary lubricant.

22. The aqueous metal working fluid of claim 17, wherein the at least one amine is selected from 1,5-dimethylhexylamine; 2-ethylhexylamine; heptylamine; octylamine; tris (2-aminoethyl)amine and combinations thereof and optionally further comprises 1,4-cyclohexanediamine and/or 2-methylpentane-1,5-diamine.

23. The aqueous metal working fluid of claim 17, wherein the at least one *Mycobacterium*-inhibitory amine is selected from the group consisting of amines of Formula (Ia), (Ic) and combinations thereof:

wherein each $R_1$ is independently $C_5$-$C_{10}$ alkyl, or $(NH_2CH_2CH_2)_3N$,   Formula Ic:

present in an effective *Mycobacterium* inhibiting amount of about 2.5 wt. % to 15 wt. % of the at least one *Mycobacterium*-inhibitory amine selected from the group consisting of amines of Formula (Ia), (Ic) and combinations thereof, based on the total weight of the aqueous metal working fluid.

* * * * *